United States Patent [19]

Schoenenberger

[11] 4,165,312
[45] Aug. 21, 1979

[54] PHOSPHORYLATED NONAPEPTIDES, PROCESSES FOR THE PREPARATION THEREOF AND PHARMACEUTICAL COMPOSITIONS CONTAINING THEM

[75] Inventor: Guido A. Schoenenberger, Reinach, Switzerland

[73] Assignee: Hoffmann-La Roche Inc., Nutley, N.J.

[21] Appl. No.: 919,046

[22] Filed: Jun. 26, 1978

[30] Foreign Application Priority Data

Jun. 30, 1977 [CH] Switzerland ............................ 8092/77

[51] Int. Cl.$^2$ ...................... C07C 103/52; A61K 37/00
[52] U.S. Cl. ................................ 260/112.5 R; 424/177
[58] Field of Search ................... 260/112.5 R; 424/177

[56] References Cited

U.S. PATENT DOCUMENTS 2,768,997  10/1956  Reeves et al. ................. 260/112.5 R

OTHER PUBLICATIONS

M. Monnier, et al., Experientia 33, (1976), pp. 548-552.

*Primary Examiner*—Delbert R. Phillips
*Attorney, Agent, or Firm*—Jon S. Saxe; George M. Gould

[57] ABSTRACT

Novel phosphorylated nonapeptides having the formula

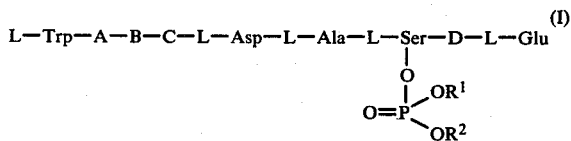

wherein
A represents L- or D-alanine,
B, C and D represent Gly or D-alanine and
$R^1$ and $R^2$ represent hydrogen or alkyl, and derivatives of compounds of formula I, wherein one or more of the amide groups is N-alkylated and/or the end amino group is acylated or mono- or dialkylated and/or at least one carboxy group of L-Asp and L-Glu is esterified, amidated or mono- or dialkylamidated or reduced to a hydroxymethyl group, wherein the hydroxy group may optionally again be acylated, phosphorylated or alkylated are disclosed. These compounds are useful in pharmaceutical compositions as sleep inducing agents. Processes for the preparation of said nonapeptides are also disclosed.

4 Claims, No Drawings

PHOSPHORYLATED NONAPEPTIDES, PROCESSES FOR THE PREPARATION THEREOF AND PHARMACEUTICAL COMPOSITIONS CONTAINING THEM

BACKGROUND OF THE INVENTION

A nonapeptide having the sequence L-Trp-L-Ala-Gly-Gly-L-Asp-L-Ala-L-Ser-Gly-L-Glu (MW=849), hereinafter referred to as DSIP (Delta-Sleep-Inducing Peptide) was isolated in the period 1971-1977 as the humoral sleep factor from the blood of rabbits, purified and characterized. Its structure was also finally elucidated (Pflügers Arch. 369, 99-101, 1977). Biological tests carried out using synthetic DSIP gave identical results in comparison with natural DSIP isolated from rabbit blood when administered intra-cerebral-ventricularly in rabbits (Experientia 33, 548, 1977). Intra-cerebral-ventricular doses of 6 nMol DSIP/kg induced a physiological effect in rabbits which on an EEG manifested itself as being equivalent to the phenomena found during natural orthodox deep sleep (Proc. Natl. Acad. Sci. USA 74, 1282-1286, 1977). Synthetically prepared DSIP was also active following intravenous administration of 30 nMol/kg in cats and rats, whereby the EEG recordings and also the passive behavioural tests showed a significant improvement in deep and paradoxal sleep. The administration of synthetic DSIP by means of an arterial perfusion on isolated rat heads also gave EEG readings which were sleep equivalent. In animal trails, methods of application which may also be used in human medicine also resulted in the induction of a natural state of sleep.

It has, however, been shown in a series of experiments, that the induction of sleep following the administration of DSIP, results in an all or nothing effect when the dosage varies by only ±20 nMol/kg body weight, that is, only the exact dosage of the correct quantity of DSIP achieves the desired effect. Furthermore, it has been found that intravenous administration requires a dosage of 6 nMol/kg which is substantially higher than that required for intra-cerebral-ventricular administration for the induction of sleep and finally, if administration is carried out by the intravenous route, there is a delay before the induction of sleep.

These differences in activity following the two types of application are not surprising, since oligopeptides of the DSIP type are known from experience to undergo rapid enzymatic degradation on intravenous (sub- or percutaneous) application and in addition do not easily penetrate the blood brain barrier.

SUMMARY OF THE INVENTION

It is an object of the instant invention to find compounds of the DSIP type which are more stable to enzymatic degradation, more easily penetrate the blood brain barrier and have improved biological and pharmacodynamic properties.

Comparative tests are set out below which show that DSIP which has been phosphorylated on the OH group of the serine and also the corresponding derivatives of DSIP analogues in which the second, third, fourth and/or eighth aminoacid radical of the sequence is a D-alanine radical, on intravenous application to rats, not only give a reduction in the dosage needed, as compared with DSIP, but also give an accentuated activity with more rapid onset and longer, that is for more hours, duration. This protracted and accentuated activity constitutes an important therapeutic advantage.

The present invention thus provides phosphorylated nonapeptides having the general formula

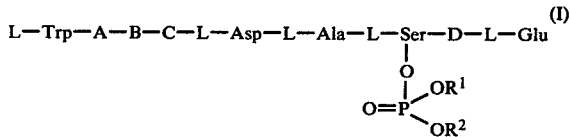

wherein
A represents L- or D-alanine,
B, C and D represent Gly or D-alanine and
$R^1$ and $R^2$ represent hydrogen or alkyl,
and derivatives of compounds of formula I, wherein one or more of the amide groups is N-alkylated and/or the end amino groups are acylated or diacylated and/or at last one carboxyl group of L-Asp and L-Glu is esterified, amidated or mono- or dialkylamidated or reduced to a hydroxymethyl group, wherein the hydroxy group may optionally again be acylated, phosphorylated or alkylated.

Preferred compounds according to the present invention are compounds of formula I itself and amongst these, those in which A represents L-alanine and B, C and D represent glycine, such as for example

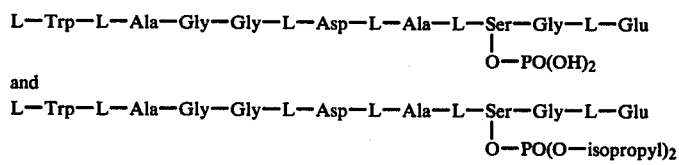

The compounds according to the present invention may be prepared by a process which is characterized in that a nonapeptide of the formula

wherein A, B, C and D have the meanings given above or a derivative of such a compound as defined above, is phosphorylated, or the protecting group(s) is/are split off from a compound of formula I, or a derivative thereof as defined above, in which at least one of the functional groups is protected.

The individual reactions which lead to the end products of the present invention and their purification as well as the preparation of the starting materials may be carried out using conventional methods, that is by using methods which are well known in peptide chemistry [see for example "Methoden der organischen Chemie" (Houben-Weyl) Vol. XV, parts 1 and 2, Georg Thieme Verlag, Stuttgart, 1974].

Thus, for example, one may use as the starting material synthetically prepared DSIP or one of its analogues, in positions 2, 3, 4 and/or 8, that is a compound of formula II, wherein the functional groups, with the exception of the OH group of serine which is to be phosphorylated, are protected. The phosphorylation may be carried out by reaction with a mono functional derivative of phosphoric acid, such as dibenzyl phosphoryl chloride or diphenyl phosphoryl chloride. The protecting groups should be so chosen that they can be removed under mild conditions which do not result in the modification of the peptide sequence. Examples of protecting groups which may be used, since they may be removed by catalytic hydrogenolysis without difficulty include N-benzyloxycarbonyl-, N-benzyl-, benzylester- and ether groups. The protected serine peptide may be phosphorylated in anhydrous pyridine using dibenzyl phosphoryl chloride. The resulting phosphate derivative is washed, purified with an aqueous acid or base and subjected to hydrogenolysis in t-butanol solution. The resulting phosphorylated peptide may be purified by means of thin layer or anion exchange chromatography. The phosphorylation of serine-containing peptides with diphenyl phosphoryl chloride is preferred in view of a selective splitting off of N-benzyloxy carbonyl- and benzylester-groups by means of palladium catalysed hydrogenolysis. For the removal of one or both phenyl groups a platinum catalyst may be used (Acta.Chem.Scan. 13, 1407 and 1422 (1959)).

On the other hand one may start by using an unprotected DSIP sequence which is phosphorylated with a mono-halogeno phosphoric acid (e.g., $ClPO(OH)_2$) or a mono-halogeno phosphoric acid ester (for example with diisopropylfluorophosphate $FPO[OCH(CH_3)_2]_2$).

EXAMPLE 1

Phosphorylation of N-benzyloxycarbonyl-DSIP-benzyl ester

A solution of N-benzyloxycarbonyl-DSIP-benzyl ester (5 nMol) dissolved in 10 ml of pyridine which as been dried over barium oxide was cooled almost to freezing. Dibenzylphosphoryl chloride which had been freshly prepared from dibenzyl was then added, the mixture was well shaken and left to stand overnight at 4° C. 75 ml of cold ethyl acetate and 75 ml of cold water was then added to the mixture, which was then centrifuged. The supernatant was then successively washed with cold water, 1 M $H_2SO_4,H_2O$, saturated $NaHCO_3$ solution and water and dried over anhydrous $Na_2SO_4$. The phosphate ester of the protected peptide was obtained in solid form after vacuum distillation of the solvent. The solid was then dissolved in a mixture of t-butanol/water and hydrogenated using 10% Pd/C. The reaction mixture was filtered, the catalyst and the filtrate washed with water and the combined washings evaporated to dryness under a vacuum. The so obtained DSIP which was phosphorylated on the hydroxy group of the serine

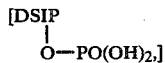

was purified using thin layer chromatography or an anion exchanger (Acta Chem. Scan. 15, 163 (1961).

EXAMPLE 2

Phosphorylation of DSIP 5 mg of DSIP and 1 mg of L-tryptophan was mixed with 1 ml of phosphorous oxytrichloride at 5° C. The mixture was dissolved in 100 ml of concentrated formic acid and stirred for 8 hours at 0° C. with the exclusion of moisture. The product was then lyophylized over NaOH under a high vacuum. After the addition of 2 ml of ice water the pH of the solution was adjusted to 8 at 0° C. using 1 N NaOH. This pH was maintained constant for 2 hours. The solution was again lyophylized and the resulting lyophylisate was dissolved in 0.5 ml water. 100 μl portions of this solution were applied to a Silica gel plate (layer thickness 2 mm, free from binding agent) and developed over eight hours at room temperature with acetone/water (7:3, v/v). The plate, apart from a strip round the edge was covered with aluminum foil and sprayed with florescamine solution (0.2% in acetone). Using UV light it was thus possible to fix the positions of the bands containing the desired material (Rf 0.47). These were scraped off and eluted with water. The supernatant resulting from the centrifugation of the eluate at 25,000 g was lyophylized. The so obtained material was dissolved in 0.5 ml $H_2O$ and loaded on to a Sephadex-G 15 column (145 ml) which was then eluted with water. Fractions of 1 ml were collected. The fractions which showed UV absorption at 280 nm were collected and lyophylized. The so purified and lyophylized material

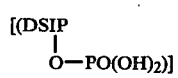

was used for the rising test in rats (J. Biol. Chem. 202, 67 (1953)).

EXAMPLE 3

Phosphorylation of DSIP 10 mg of DSIP were dissolved in 0.5 ml of water and 0.1 ml of 1 M phosphate buffer pH 7.3. A 20 molar excess of di-isopropylfluorophosphate was added to this solution which was then well stirred at room temperature for 30 minutes. A further 100 μl of 1 M phosphate buffer (pH 7.3) were then added to this mixture which was then allowed to stand for a further 4 hours at room temperature. The mixture was then loaded on to a Sephadex-G 15 column (145 ml) and eluted with water at room temperature. 100 fractions of 1.5 ml each were collected. The fractions which contained the phosphorylated DSIP

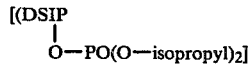

(Nos. 35–45) were purified and lyophylized. The material was then used directly for the rising test in rats.

EXAMPLE 4

20 mg of DSIP (23.5 μMol) in 3 ml of phosphorous oxytrichloride was dissolved in 500 μl of formic acid at 0° C. The reaction mixture was then stirred at 0° C. for 200 hours with the complete exclusion of moisture. Excess phosphorous oxytrichloride and formic acid were then removed under high vacuum. For the removal of the chlorine atom of the phosphate ester radical the material was dissolved in 5 ml of ice water and stirred at pH 8 for 2 hours at 0–4° C. The material was finally lyophylized.

The lyophylized crude product was then dissolved in 1.2 ml water and applied to 6 plates for preparative thin layer chromatography (Silica gel), in each case 2 cm from the edge of the plate. Development was carried out for eight hours at room temperature using acetone/water (7:3, v/v). The plates were covered with aluminum foil apart from a strip round the edge 3 cm wide and sprayed with Florescamine solution (0.2% in acetone). Illumination of the plates with UV light at 350 nm showed specs round the edge. The bands having an Rf value of 0.6 were indicated, removed and eluted with 5 ml water. The eluates were centrifuged at 20,000 g for 10 minutes and the supernatant was lyophylized.

The lyophylized peptide was dissolved in 2 ml water, loaded on to a Sephadex G-15 column (220 ml) and eluted with water.

The evaluation of the fractions was carried out using UV light at 280 nm and showed a peak with a flat shoulder. The fractions belonging to the peak were divided into 3 pools and lyophylized separately. The substances from pools 1 and 2 were chromatographed on Sephadex G 15 and again lyophylized.

The material of pool 1 was identified as practically 100% DSIP phosphorylated on the OH group of the serine. It had an Rf value on Silica gel plates in a water-/acetone (7:3, v/v) system of 0.42. The non-phosphorylated starting material showed under similar conditions a Rf value of 0.87. Yield 25%.

Determination of biological activity in the rising test

In a randomised double blind study the vigilant state in 8 test rats and 8 control animals was simultaneously quantified. In the rising test, each rising of a test animal was counted as a point. The experiment was carried out 90 minutes after the intravenous injection of the substance (Test, T) in 0.2 ml NaCl solution or of 0.2 ml of NaCl solution alone (Control C), for 3 hours during the alert period of the rats before midnight. The counting was done by three unbiased people, again under randomised double blind conditions. The frequency of the rising of the control animals was set at 100% and the reduction of the number of risings of the test animals is calculated. The results are summarized in the following table.

| No. | Dose [nMol/kg] | Compound | C (%) | T (%) |
|---|---|---|---|---|
| 1 | 90 | DSIP | 100 | 54 |
| 2 | 10 | DSIP $\underset{O-PO(OH)_2}{\|}$ *) | 100 | 45 |
| 3 | 30 | DSIP $\underset{O-PO(O-isopropyl)_2}{\|}$ *) | 100 | 50 |

Test versus Control p <0.001
*Phosphorylation on serine radical.

The compounds of this invention may be used in pharmaceutical preparations, having a direct or delayed release of the active ingredient, in admixture with suitable organic or inorganic inert carrier materials which are suitable for enteral or parenteral administration, such as for example water, gelatine, gum arabic, lactose, starches, magnesium stearate, talc, vegetable oils, polyalkyleneglycols or petroleum jelly. The pharmaceutical preparations may be in solid form such as for example tablets, dragees or capsules, or in liquid form, for example as solutions, suspensions or emulsions. If desired they may be sterilised and/or contain further auxiliary substances such as preserving agents, stabilising agents, wetting or emulsifying agents, agents for improving taste, salts for varying the osmotic pressure or buffers. The preparation of the pharmaceutical compositions may be carried out in a conventional manner.

I claim:

1. A phosphorylated nonapeptide of the formula

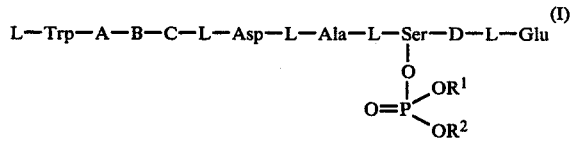

wherein
A represents L- or D-alanine,
B, C and D represent Gly or D-alanine, and
$R^1$ and $R^2$ represent hydrogen or alkyl.

2. A phosphorylated nonapeptide as claimed in claim 1 of the formula

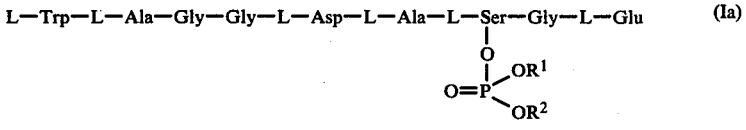

wherein $R^1$ and $R^2$ represent hydrogen or alkyl.

3. A compound of claim 1 wherein said compound is

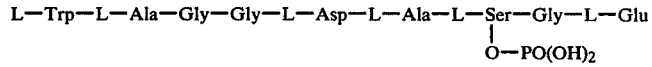

4. A compound of claim 1 wherein said compound is

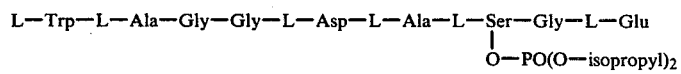

* * * * *